(12) United States Patent
Liu

(10) Patent No.: US 10,912,531 B2
(45) Date of Patent: Feb. 9, 2021

(54) SYSTEM AND METHOD FOR CREATING A THREE-DIMENSIONAL BONE IMAGE OF A BONE

(71) Applicant: Chi Mei Medical Center, Tainan (TW)

(72) Inventor: Ching-Feng Liu, Kaohsiung (TW)

(73) Assignee: Chi Mei Medical Center, Tainan (TW)

(*) Notice: Subject to any disclaimer, the term of this patent is extended or adjusted under 35 U.S.C. 154(b) by 152 days.

(21) Appl. No.: 16/210,463

(22) Filed: Dec. 5, 2018

(65) Prior Publication Data
US 2019/0167222 A1   Jun. 6, 2019

(30) Foreign Application Priority Data

Dec. 6, 2017   (TW) .............................. 106142744 A

(51) Int. Cl.
| | |
|---|---|
| *A61B 6/00* | (2006.01) |
| *A61B 6/03* | (2006.01) |
| *A61B 34/10* | (2016.01) |
| *G16H 30/40* | (2018.01) |
| *G16H 50/50* | (2018.01) |

(52) U.S. Cl.
CPC .............. *A61B 6/5235* (2013.01); *A61B 6/03* (2013.01); *A61B 6/466* (2013.01); *A61B 34/10* (2016.02); *G16H 30/40* (2018.01); *G16H 50/50* (2018.01); *A61B 6/505* (2013.01); *A61B 2034/105* (2016.02)

(58) Field of Classification Search
CPC ......... A61B 6/5235; A61B 6/03; A61B 34/10; A61B 6/466; A61B 2034/105; A61B 6/505; A61B 6/5217; A61B 6/501; A61B 6/032; G16H 50/50; G16H 30/40

See application file for complete search history.

(56) References Cited

U.S. PATENT DOCUMENTS

| | | | |
|---|---|---|---|
| 10,217,238 B2* | 2/2019 | Ostrovsky-Berman | ...................... G06T 7/62 |
| 2005/0203367 A1* | 9/2005 | Ahmed | .................. A61B 90/36 600/407 |
| 2008/0260219 A1* | 10/2008 | Witte | ...................... G06F 19/00 382/128 |
| 2010/0080434 A1* | 4/2010 | Seifert | .................... G06T 7/143 382/131 |
| 2017/0330319 A1* | 11/2017 | Xu | ............................ G06T 7/73 |

* cited by examiner

*Primary Examiner* — Brandon J Miller
(74) *Attorney, Agent, or Firm* — Muncy, Geissler, Olds & Lowe, P.C.

(57) ABSTRACT

A system for creating a three-dimensional (3D) bone image of a bone is used with a 3D bone model of the bone that includes a plurality of bony landmarks. The system includes a 3D scanning device to scan the bone and generate a bone contour image, and an image processing device. The image processing device processes the 3D bone model to obtain a plurality of spatial locations respectively of the bony landmarks, and processes the bone contour image to identify a plurality of features that correspond respectively with the bony landmarks and to obtain a plurality of spatial locations respectively of the features. The image processing device performs image registration for the 3D bone model and the bone contour image, so as to create the 3D bone image by proportionally overlapping the 3D bone model and the bone contour image.

19 Claims, 8 Drawing Sheets

SYSTEM AND METHOD FOR CREATING A THREE-DIMENSIONAL BONE IMAGE OF A BONE

CROSS-REFERENCE TO RELATED APPLICATION

This application claims priority of Taiwanese Patent Application No. 106142744, filed on Dec. 6, 2017.

FIELD

The disclosure relates to a system and a method for creating a three-dimensional bone image of a bone to assist orthopedics surgery.

BACKGROUND

Temporal bones are among many bones that constitute the skull, and house many structures of the ears (i.e., the outer ear, the middle ear, the inner ear, the vestibular system, the facial nerve (CN VII), and blood vessels, etc.).

An orthopedics surgery on the temporal bones involves employing an electrical drill to drill one of the temporal bones. However, the surgery has to be operated with extra care with respect to the above structures of the ears, as any wounds on the above structures of the ears inflicted by the electrical drill may cause serious, sometimes fatal complications.

Conventionally, for a temporal bone surgery, a three-dimensional image model of the skull of a patient is created using computed tomography (CT). A doctor then performs an analysis of the three-dimensional image model to determine apart of the temporal bone that shows symptom and determine a spatial relation between the part of the temporal bone and the structures of the ears (e.g., relative locations, distances, etc.). Afterward, the doctor may then perform the temporal bone surgery to drill the part of the temporal bone. With the knowledge of the spatial relation and other clues, such as an appearance of a part of the temporal bone that has been drilled, and a shape of the part of the temporal bone that has been exposed upon drilling, the doctor may be able to determine aspects of the drilling such as a depth, a direction in which the drilling should be continued, and whether the drill should be replaced with another tool.

SUMMARY

Therefore, one object of the disclosure is to provide a system for creating a three-dimensional (3D) bone image of a bone to assist orthopedics surgery.

According to the disclosure, the system is used with a 3D bone model of the bone. The 3D bone model is constructed by scanning the bone using X-ray computed tomography. The 3D bone model includes a plurality of bony landmarks. The system includes:

a 3D scanning device to scan the bone and to generate a bone contour image; and an image processing device that is coupled to the 3D scanning device for receiving the bone contour image, and that includes a positioning unit to process the 3D bone model so as to obtain a plurality of spatial locations respectively of the bony landmarks, and to process the bone contour image so as to identify a plurality of features that correspond respectively with the bony landmarks and to obtain a plurality of spatial locations respectively of the features, an image alignment unit to perform image registration for the 3D bone model and the bone contour image by aligning the spatial locations of the bony landmarks respectively with the spatial locations of the features, so as to create the 3D bone image by proportionally overlapping the 3D bone model and the bone contour image, and a display unit to display the 3D bone image.

Another object of the disclosure is to provide a method for creating a three-dimensional bone image of a bone to assist orthopedics surgery.

According to one embodiment of the disclosure, the method is implemented by a system used with a 3D bone model of the bone. The 3D bone model is constructed based on a bone using X-ray computed tomography. The system includes a three-dimensional scanning device and an image processing device. The 3D bone model includes a plurality of bony landmarks. The method includes:

processing, by the image processing device, the 3D bone model to obtain a plurality of spatial location for the bony landmarks, respectively;

scanning, by the 3D scanning device, the bone to generate a bone contour image;

processing, by the image processing device, the bone contour image so as to identify a plurality of features that correspond respectively with the bony landmarks, and obtain a plurality of spatial locations respectively of the features; and performing, by the image processing device, image registration for the 3D bone model and the bone contour image by aligning the spatial locations of the bony landmarks respectively with the spatial locations of the features, so as to create the 3D bone image by proportionally overlapping the 3D bone model and the bone contour image.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
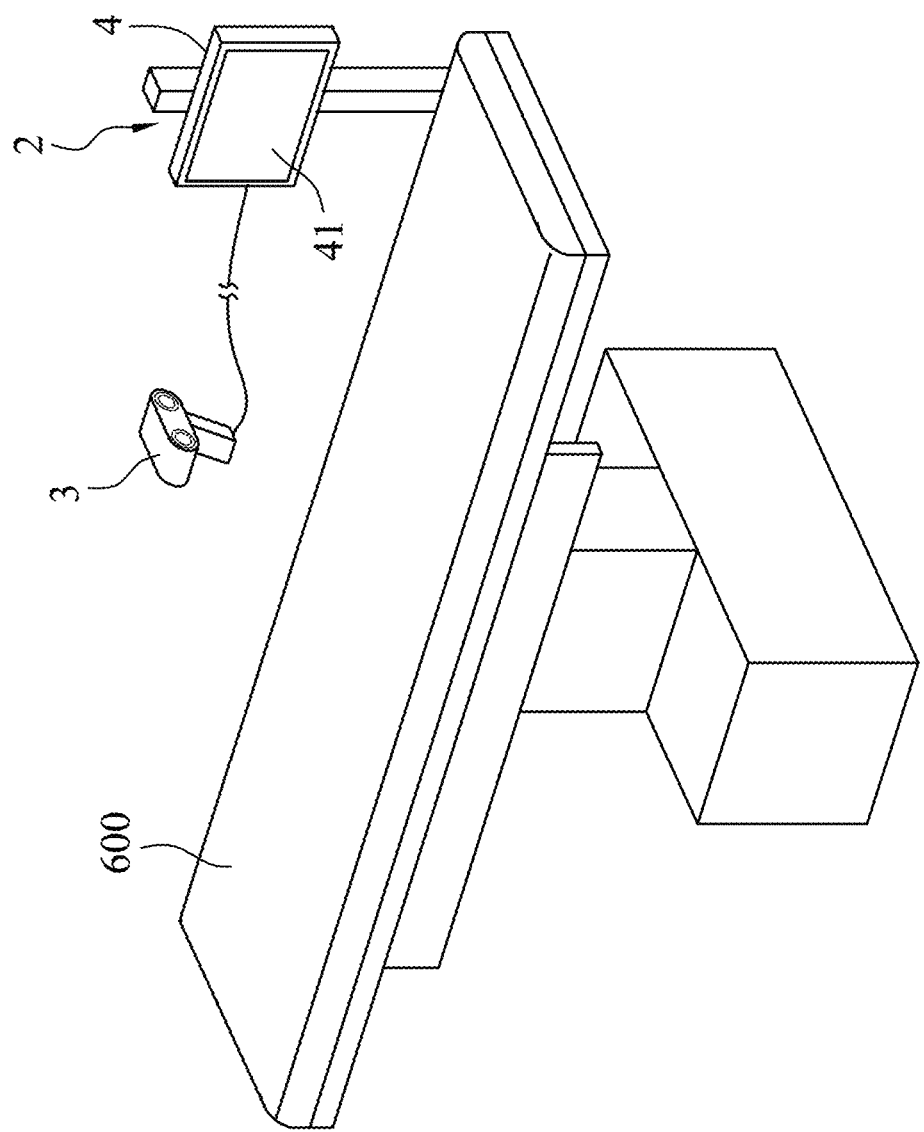
FIG. 1 is a schematic view illustrating a system for creating a three-dimensional bone image of a bone according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

FIG. 1 is a schematic view illustrating a system 2 for creating a three-dimensional bone image of a bone according to one embodiment of the disclosure.

In this embodiment, the system 2 is disposed on an operating table 600, and includes a three-dimensional (3D) scanning device 3 and an image processing device 4.

Figure 3:
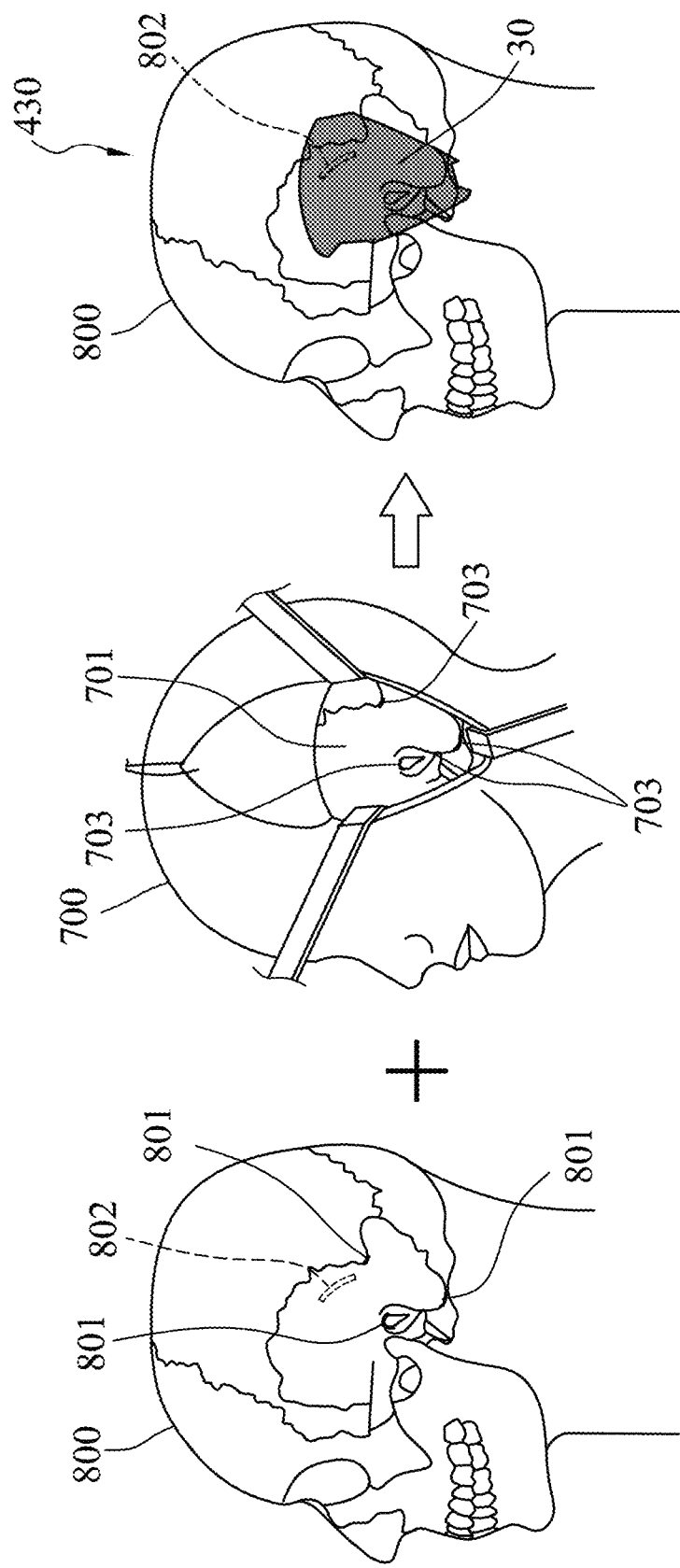
FIG. 3 illustrates a three-dimensional (3D) bone model of a bone and a bone contour image being proportionally overlapped to create a 3D bone image.

Further referring to FIG. 3, in this embodiment, the system 2 is configured for creating a three-dimensional bone image 430 of a bone 701 to assist orthopedics surgery, such as a temporal bone surgery.

The system 2 to be used with a 3D bone model 800 of the bone 701 that may be constructed by scanning the bone 701 using X-ray computed tomography (CT). In this embodiment, the 3D bone model 800 is constructed with respect to a skull of a patient, and the bone 701 is a temporal bone. It is noted that the construction of the 3D bone model 800 may be done in a manner that is known in the art, and therefore details regarding the construction of the 3D bone model 800 are omitted herein for the sake of brevity.

The 3D bone model 800 includes a plurality of bony landmarks 801 and an image of underlying structure 802.

The bony landmarks 801 relate to features of the bone 701, and are exposed and visually identifiable.

The image of underlying structure 802 corresponds with a part of the bone 701, and shows structures that are covered by the part of the bone 701 (e.g., facial nerves, meninges, blood vessels, etc.).

The bone 701 may be disposed with a plurality of positioning components 703 that correspond respectively with the bony landmarks 801. The positioning components 703 may each be embodied using a sticker, a block, etc.

Figure 4:
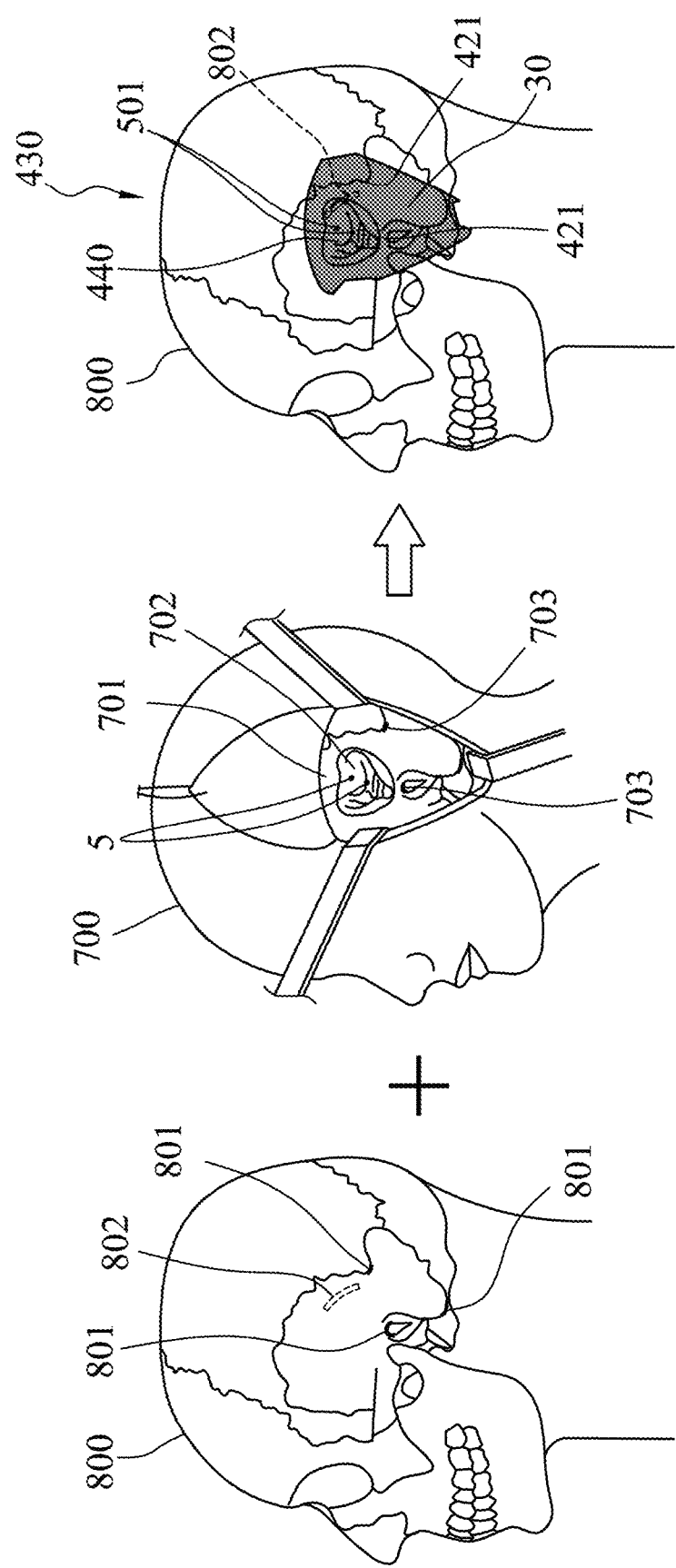
FIG. 4 illustrates a three-dimensional (3D) bone model of a bone and a bone contour image being proportionally overlapped to create a 3D bone image, the bone having a depressed area due to an orthopedics surgery.
Figure 5:
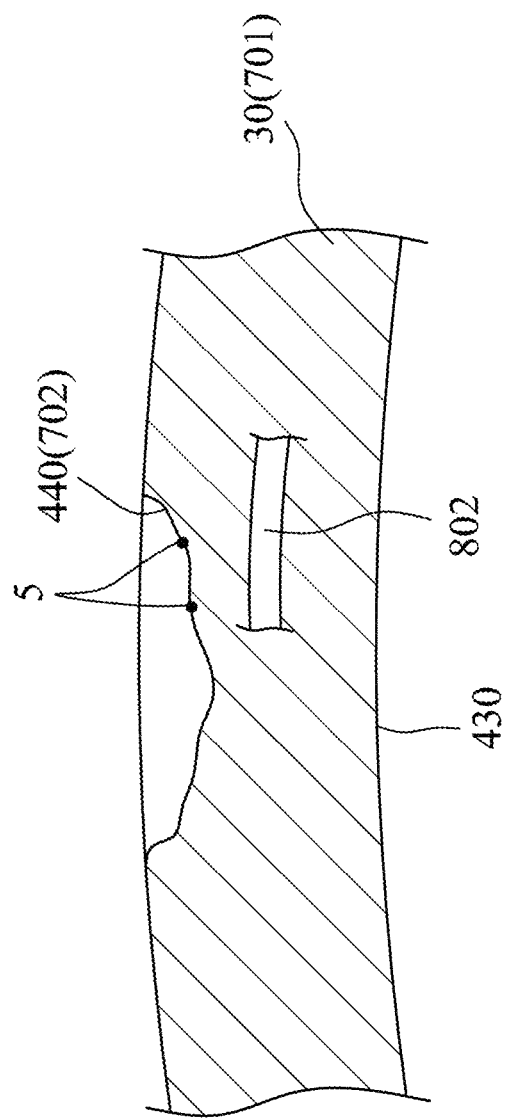
FIG. 5 is a fragmentary sectional view of an exemplary 3D bone image including an image of underlying structure.

Referring to FIGS. 4 and 5, in this embodiment, the bone 701 is partly exposed for performing the orthopedics surgery, and is formed with a depressed area 702 during the orthopedics surgery. The depressed area 702 of the bone 701 may be placed with a plurality of tagging components 5 for identifying spots on the depressed area 702 that need more information on the structures covered thereby. The tagging components 5 may each be embodied using a sticker, a block, etc.

The 3D scanning device 3 may be operated by relevant personnel (e.g., an operating doctor, an assistant, etc.) to scan the bone 701, so as to generate a bone contour image 30 of the bone 701. It is noted that the 3D scanning device 3 can detect the positioning components 703 and the tagging components 5. Accordingly, when the positioning components 703 are placed on the bone 701 and/or the tagging components 5 are disposed on the depressed area 702, the bone contour image 30 contains images of the positioning components 703 and/or the tagging components 5.

It is noted that the operations of the 3D scanning device 3 to generate the bone contour image 30 may be done in a manner that is known in the art, and therefore details thereof are omitted herein for the sake of brevity.

Figure 2:
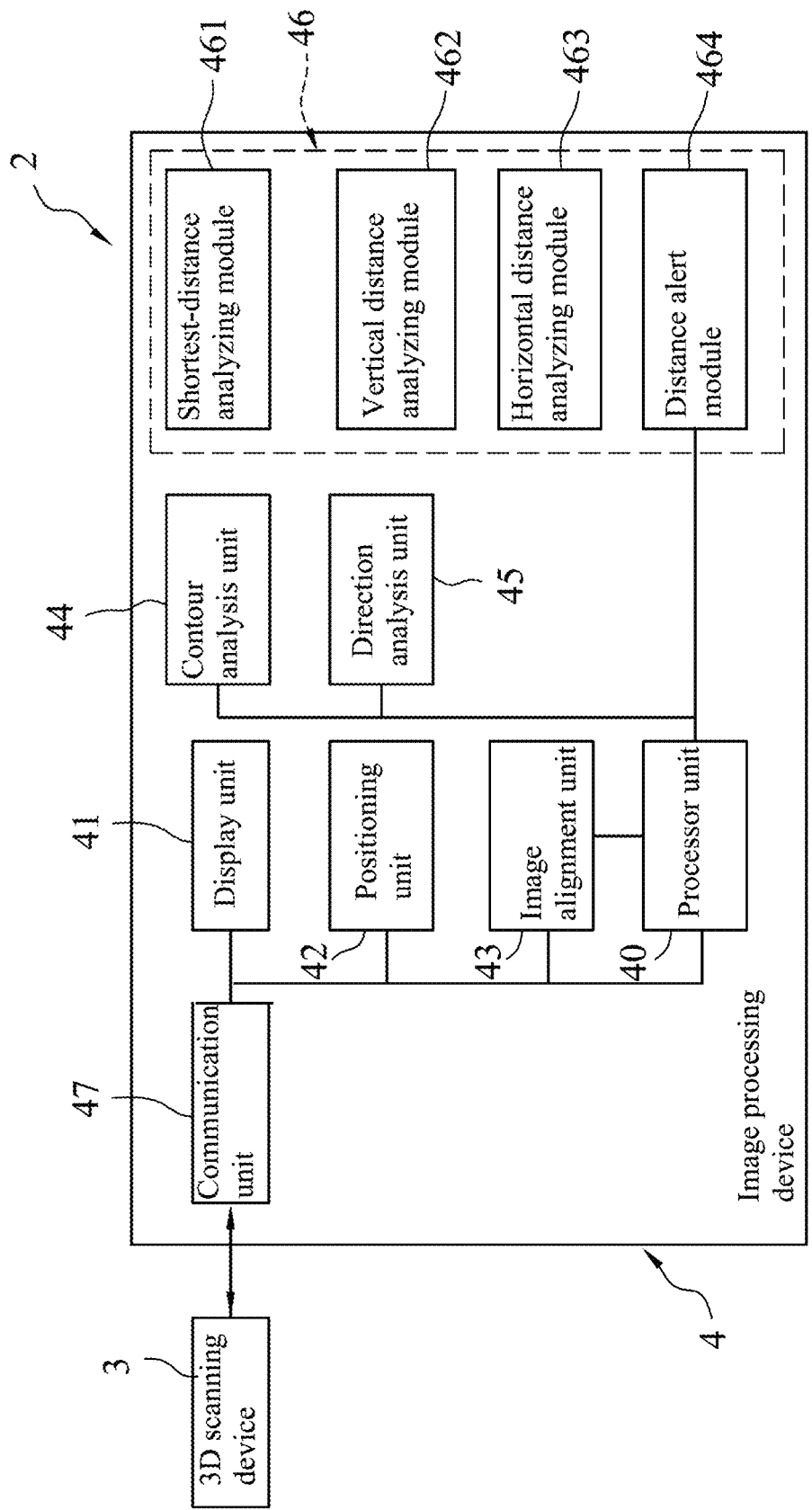
FIG. 2 is a block diagram illustrating components of the system, according to one embodiment of the disclosure.

FIG. 2 is a block diagram illustrating components of the system 2 according to one embodiment of the disclosure.

The image processing device 4 may be embodied using a computing device (e.g., a personal computer, a laptop, a tablet, a mobile device, etc.), and includes a processor unit 40, a display unit 41, a positioning unit 42, an image alignment unit 43, a contour analysis unit 44, a direction analysis unit 45, a distance analysis unit 46 and a communication unit 47.

The processor unit 40 may include, but not limited to, a single core processor, a multi-core processor, a dual-core mobile processor, a microprocessor, a microcontroller, a digital signal processor (DSP), a field-programmable gate array (FPGA), an application specific integrated circuit (ASIC), a radio-frequency integrated circuit (RFIC), and/or the like for performing operations that are to be described in the succeeding paragraphs.

It is noted that in this embodiment, the components of the image processing device 4 (i.e., the positioning unit 42, the image alignment unit 43, the contour analysis unit 44, the direction analysis unit 45 and the distance analysis unit 46) may be embodied using hardware circuitry or software that is stored in the image processing device 4 and executed by the processor unit 40.

The communication unit 47 may include a wired connection socket, a short-range wireless communicating module supporting a short-range wireless communication network using a wireless technology of Bluetooth® and/or Wi-Fi, etc., and a mobile communicating module supporting telecommunication using Long-Term Evolution (LTE), the third generation (3G) and/or fourth generation (4G) of wireless mobile telecommunications technology, and/or the like. The communication unit 47 is capable of connecting with the 3D scanning device 3 for receiving the bone contour image 30 and connecting with, for example, CT equipment for obtaining the 3D bone model 800.

The positioning unit 42 is controlled by the processor unit 40 to process the 3D bone model 800 so as to obtain a plurality of spatial locations respectively of the bony landmarks 801. In this embodiment, the spatial locations may be expressed in the form of sets of coordinates.

The positioning unit 42 is controlled by the processor unit 40 to further process the bone contour image 30 so as to identify a plurality of features 421 that correspond respectively with the bony landmarks 801, and so as to obtain a plurality of spatial locations respectively of the features 421 (see FIG. 4).

In one example, when the bone 701 is placed with a plurality of positioning components 703 that correspond respectively with the bony landmarks 801, the positioning unit 42 is configured to obtain the spatial locations of the features 421 based on locations respectively of the positioning components 703.

In another example, the positioning unit 42 is configured to identify the features 421 by analyzing the bone contour image 30 according to shapes respectively of the bony landmarks 801.

When the bone contour image 30 contains the images of the tagging components 5, the positioning unit 42 further identifies a plurality of tagging points 501 (see FIG. 4) that correspond respectively with the tagging components 5, and obtains a plurality of spatial locations respectively of the tagging points 501.

The image alignment unit 43 is controlled by the processor unit 40 to perform image registration for the 3D bone model 800 and the bone contour image 30. Specifically, the image alignment unit 43 performs the image registration by aligning the spatial locations of the bony landmarks 801 respectively with the spatial locations of the features 421, so as to create the 3D bone image 430 by proportionally overlapping the 3D bone model 800 and the bone contour image 30 (see FIG. 4).

The 3D bone image 430 may be displayed on the display unit 41 for viewing by the personnel, and is operable in various ways (e.g., move, rotate, zoomed in and out, etc.).

As shown in FIGS. 4 and 5, the 3D bone image 430 shows a current appearance of the bone 701 and the image of underlying structure 802 that overlaps the bone contour image 30. Furthermore, the 3D bone image 430 may show the feature(s) 421 and the tagging point(s) 501.

The contour analysis unit 44 is configured to process the bone contour image 30 so as to indicate an operation surface 440 corresponding with a contour of the depressed area 702 on the 3D bone image 430.

In this embodiment, the 3D scanning device 3 may be operated to scan the bone 701 multiple times during the course of the orthopedics surgery, so as to generate multiple bone contour images 30 showing the bone 701 in different shapes. The contour analysis unit 44 is configured to process the bone contour images 30 so as to obtain a more accurate indication of the operation surface 440. The operation surface 440 is then dynamically indicated in the 3D bone image 430.

In some embodiments, the contour analysis unit 44 may be configured to partition the operation surface 440 into a plurality of monitoring sectors (not depicted in the drawings).

The direction analysis unit 45 is configured to determine a direction of the image of underlying structure 802 with respect to the operation surface 440 indicated in the 3D bone image 430. Furthermore, the direction analysis unit 45 is configured to generate direction data regarding the direction of the image of underlying structure 802.

Specifically, the direction data may be in the form of multiple sets of coordinates that correspond respectively with different spots on the image of underlying structure 802 with reference to a preset reference point in a hypothetical 3D coordination system, and a plurality of sets of coordinates that correspond respectively with different spots on the operation surface 440. The direction analysis unit 45 is configured to determine the direction of the image of underlying structure 802 with respect to the operation surface 440 using the direction data.

The distance analysis unit 46 is configured to determine distance data regarding at lease one distance between the image of underlying structure 802 and the operation surface 400, based on the direction data (i.e., the sets of coordinates) generated by the direction analysis unit 45.

In this embodiment, the distance analysis unit 46 includes a shortest-distance analyzing module 461, a vertical distance analyzing module 462, a horizontal distance analyzing module 463, and a distance alert module 464.

The shortest-distance analyzing module 461 is configured to obtain a plurality of shortest distances between the image of underlying structure 802 and the operation surface 400 respectively from the monitoring sectors, and the distance data includes the shortest distances. For example, for each of the monitoring sectors that is obtained by the contour analysis unit partitioning the operation surface 440, the shortest-distance analyzing module 461 calculates one shortest distance to be included in the distance data.

In a case that the tagging components 5 are placed on the depressed area 702, the shortest-distance analyzing module 461 further calculates one shortest distance between each of the tagging components 5 and the image of underlying structure 802.

The vertical distance analyzing module 462 is configured to obtain a plurality of vertical distances between the image of underlying structure 802 and the operation surface 440 respectively from the monitoring sectors. For example, for each of the monitoring sectors, the vertical distance analyzing module 462 calculates one shortest vertical distance to be included in the distance data.

In the case that the tagging components 5 are placed on the depressed area 702, the vertical distance analyzing module 462 further calculates one shortest vertical distance between each of the tagging components 5 and the image of underlying structure 802.

The horizontal distance analyzing module 463 is configured to obtain a plurality of horizontal distances between the image of underlying structure 802 and the operation surface 440 respectively from the monitoring sectors. For example, for each of the monitoring sectors, the horizontal distance analyzing module 463 calculates one shortest horizontal distance to be included in the distance data.

In the case that the tagging components 5 are placed on the depressed area 702, the horizontal distance analyzing module 463 further calculates one shortest horizontal distance between each of the tagging components 5 and the image of underlying structure 802.

It is noted that the operations of the vertical distance analyzing module 462 and the horizontal distance analyzing module 463 regarding calculation of the distances may be similar to that of the shortest-distance analyzing module 461.

According to one embodiment of the disclosure, the distance analysis unit 46 may be configured to output the distance data to the processor unit 40, which in turn controls the display unit 41 to display at least part of the distance data. For example, the distance data displayed on the display unit 41 may include, for each of the tagging components 5, the calculated shortest distance, the calculated vertical distance, and the calculated horizontal distance with respect to the image of underlying structure 802. As such, the personnel may be directly informed of the spatial relation between each of the tagging components 5 and the image of underlying structure 802.

The distance alert module 464 is configured to compare the shortest distances with an alert distance that can be preset by the personnel.

Furthermore, the distance alert module 464 is operable by the personnel to activate/deactivate a shortest distance alert mode. When the shortest distance alert mode is activated, the distance alert module 464 is configured to display, for each of the monitoring sectors, a visible cue on the monitoring sector when the shortest distance corresponding thereto is smaller than the preset alert distance.

In one example, the visible cue uses different colors and/or different brightness intensities to indicate different values of the shortest distance between the monitoring sector and the image of underlying structure 802.

Similarly, the distance alert module 464 is operable by the personnel to individually activate/deactivate vertical and horizontal distance alert modes.

When either the vertical or horizontal distance alert mode is activated, the distance alert module 464 is configured to display, for each of the monitoring sectors, a visible cue on the monitoring sector when the vertical/horizontal distance corresponding thereto is smaller than the preset alert distance. In some examples, different preset alert distances may be used in the vertical and horizontal distance alert modes. In one example, the visible cue uses different colors and/or different brightness intensities to indicate different values of the vertical/horizontal distance between the monitoring sector and the image of underlying structure 802.

Additionally, different colors and/or brightness may be applied to respective visible cues for the vertical and horizontal distance alert modes.

Figure 6:
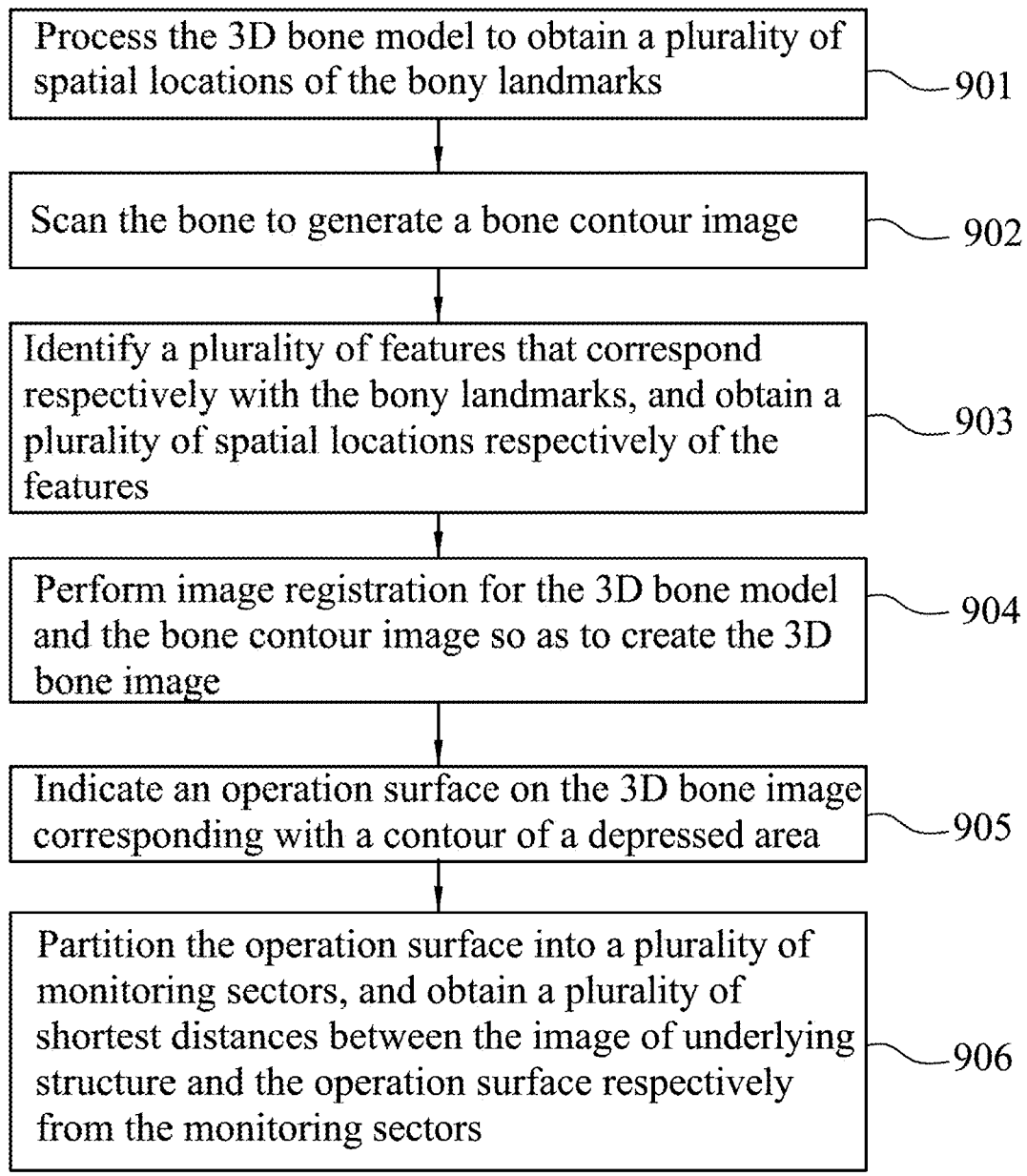
FIG. 6 is a flow chart illustrating a method for creating a 3D bone image of a bone to assist orthopedics surgery according to one embodiment of the disclosure.

FIG. 6 is a flow chart illustrating a method for creating a three-dimensional bone image 430 of a bone 701 to assist orthopedics surgery according to one embodiment of the disclosure.

In use, the method may be implemented using the system as illustrated in FIGS. 1 and 2, during the course of an orthopedics surgery.

In step 901, the image processing device 4 processes the 3D bone model 800 to obtain a plurality of spatial locations of the bony landmarks 801, respectively. In this embodiment, the bony landmarks 801 are defined as a part of the bone 701 that may serve as a visual reference to other body structures. For a temporal bone, the bony landmarks 801 may include parts corresponding with an edge of the external auditory meatus (EAM), a mastoid part of the temporal bone, a vaginal process of the temporal bone, etc.

In step 902, the 3D scanning device 3 scans the bone 701 to generate a bone contour image 30. It is noted that during the course of the orthopedics surgery, the personnel may place the positioning components 703 on the bone 701 to correspond respectively with the bony landmarks 801 before performing step 902. The bone contour image 30 may be displayed on the display unit 41 upon generation.

In step 903, the image processing device 4 processes the bone contour image 30 so as to identify a plurality of features 421 that correspond respectively with the bony landmarks 801, and obtains a plurality of spatial locations respectively of the features 421.

In one example, the image processing device 4 is configured to obtain the spatial locations of the features 421 based on locations respectively of the positioning components 703. In another example, the processing of the bone contour image 30 includes identifying the features 421 by analyzing the bone contour image 30 according to shapes respectively of the bony landmarks 801. In another example, the image processing device 4 displays the bone contour image 30, and in response to a user-input marking signal on a spot of the display unit 41 indicating one of the features 421, obtains a spatial location on the bone contour image 30 corresponding with the spot of the display unit 41 as the spatial location of the one of the features 421.

In step 904, the image processing device 4 performs image registration for the 3D bone model 800 and the bone contour image 30 by aligning the spatial locations of the bony landmarks 801 respectively with the spatial locations of the features 421, so as to create the 3D bone image 430 by proportionally overlapping the 3D bone model 800 and the bone contour image 30. As shown in FIG. 4, the image of underlying structure 802 included in the 3D bone model 800 may be displayed on the bone contour image 30.

It is noted that in different cases, the image of underlying structure 802 may be displayed in different manners. For example, in FIG. 3, a contour of the image of underlying structure 802 is displayed in broken lines, while in FIG. 4, the image of underlying structure 802 maybe displayed in a perspective manner (the actual details of the underlying structure are not necessary to describing the embodiment, and therefore are omitted).

In this embodiment, during the course of the orthopedics surgery, the previous steps may be performed multiple times (e.g., periodically).

In step 905, the image processing device 4 processes the bone contour image(s) 30, so as to indicate an operation surface 440 on the 3D bone image 430 corresponding with a contour of a depressed area 702 on the bone 701, generated due to the orthopedics surgery. In this embodiment, the operation surface 440 is determined by processing a plurality of the bone contour images 30.

Furthermore, the image processing device 4 determines a direction of the image of underlying structure 802 with respect to the operation surface 440, and generates direction data regarding the direction of the image of underlying structure 802.

In step 906, the image processing device 4 partitions the operation surface 440 into a plurality of monitoring sectors, and obtains a plurality of shortest distances between the image of underlying structure 802 and the operation surface 440 respectively from the monitoring sectors, to be included in distance data. Furthermore, the image processing device 4 compares the shortest distances with a preset alert distance, and displays, for each of the monitoring sectors, a visible cue on the monitoring sector when the shortest distance corresponding thereto is smaller than the preset alert distance.

In some embodiments, the image processing device 4 further obtains a plurality of vertical distances between the image of underlying structure 802 and the operation surface respectively from the monitoring sectors, or a plurality of horizontal distances between the image of underlying structure 802 and the operation surface 440 respectively from the monitoring sectors, and the distance data includes the vertical or horizontal distances.

Furthermore, the image processing device 4 compares each of the vertical distances and the horizontal distances with a preset alert distance, and displays, for each of the monitoring sectors, a visible cue on the monitoring sector when one of the vertical distance and the horizontal distance corresponding thereto is smaller than the preset alert distance.

It is noted that during the course of the orthopedics surgery, whenever the personnel intends to be informed of a distance between any spot of the operation surface 440 and the image of underlying structure 802, the personnel may place one tagging component 5 at the spot, and operate the system 2 to repeat the above method, so as to create a new 3D bone image that includes the corresponding tagging point 501.

Figure 7:
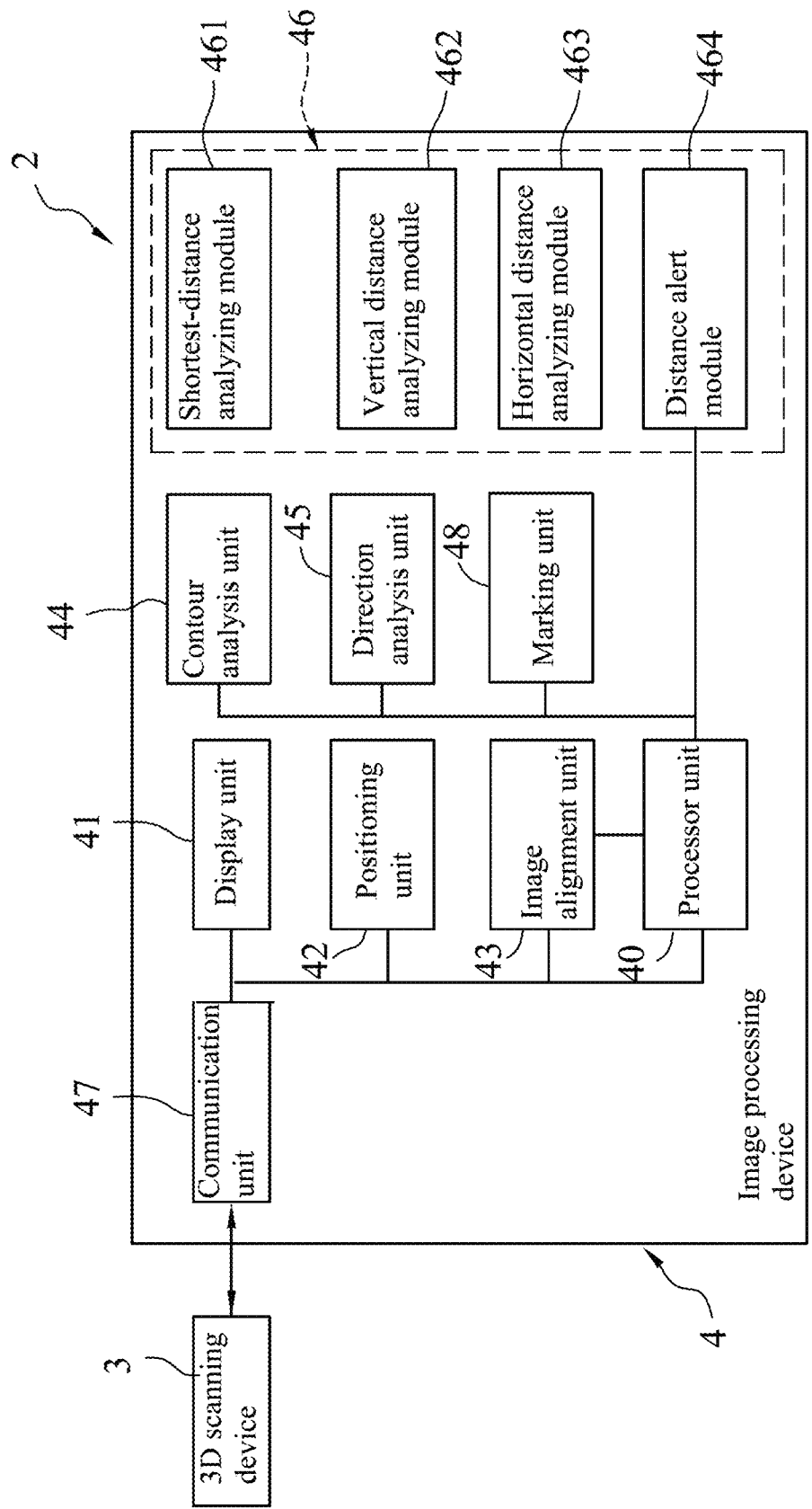
FIG. 7 is a block diagram illustrating components of the system according to one embodiment of the disclosure.

FIG. 7 is a block diagram illustrating a system 2 for creating a three-dimensional (3D) bone image 430 (see FIG. 4) of a bone 701 (see FIG. 3) according to one embodiment of the disclosure.

This embodiment differs from the embodiment of FIG. 2 in that the image processing device 4 further includes a marking unit 48 that is user-operable to mark the features 421 on the bone contour image 30 (see FIG. 4) displayed by the display unit 41.

In one example, the marking unit 48 is integrated with the display unit 41 in the form of a touch screen, and the personnel may use a finger, a stylus pen or other objects to touch the part of the touch screen so as to mark the features 421. In other examples, the marking unit 48 may be embodied using a keyboard/mouse set that is connected to or built in the image processing device 4.

Figure 8:
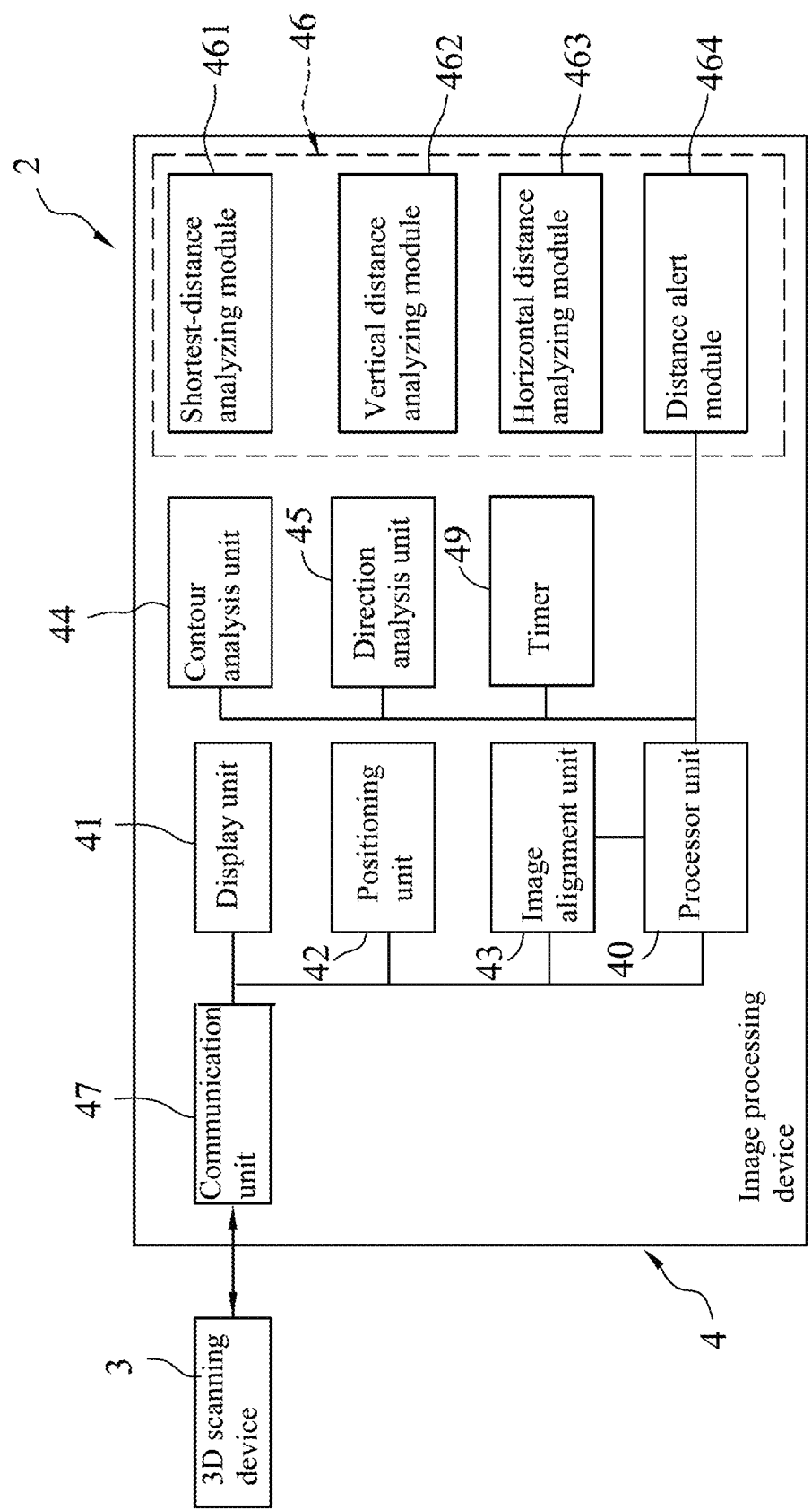
FIG. 8 is a block diagram illustrating components of the system according to one embodiment of the disclosure.

FIG. 8 is a block diagram illustrating a system 2 for creating a three-dimensional (3D) bone image 430 of a bone 701 according to one embodiment of the disclosure.

This embodiment differs from the embodiment of FIG. 2 in that the image processing device 4 further includes a timer 49 that is configured to control the 3D scanning device 3 to periodically scan the bone 701 and to generate a plurality of the bone contour images 30, and to control the image processing device 4 to periodically create the 3D bone image 430 based on the bone contour images 30. In examples, a repeating countdown time period may be set by the personnel, such as 5 minutes, 10 minutes, 30 minutes, etc. After it is determined that the countdown time period has run out, the 3D scanning device 3 is controlled to scan the bone 701, the image processing device 4 creates the 3D bone image 430 based on the newly generated bone contour image 30, and the timer 49 starts the countdown time period again.

In some examples, when the countdown time period is about to run out (e.g., have 10 seconds, 30 seconds or 1 minute remaining, etc.), the timer 49 may generate an alert that is visible or audible to the personnel (e.g., a buzz sound). In response, the personnel may pause the orthopedics surgery and clear the depressed area 702.

In this manner, the personnel may be updated with the information regarding the spatial locations of the depressed area 702 on the bone 701 and the image of underlying structure 802 periodically, and the need to have a person holding the 3D scanning device 3 to perform further scanning operation is eliminated.

To sum up, the embodiments of the disclosure provides a system 2 and a method for creating a three-dimensional (3D) bone image 430 of a bone 701 of a patient to assist orthopedics surgery. Specifically, the system 2 and the method are capable of creating the 3D bone image 430 by proportionally overlapping the 3D bone model 800 and the bone contour image 30.

Since in an orthopedics surgery, the bone 701 may be continuously drilled or chipped to form a depressed area 702 having a shape that is changing during the course of the orthopedics surgery, personnel operating the system 2 may obtain spatial information of a selected spot on the depressed area 702 of the bone 701 with reference to other structures of the patient. When a distance between the selected spot on the depressed area 702 and an image of underlying structure becomes smaller than a preset alert distance, a visible cue may be generated to alert the personnel.

That is to say, the system 2 and the method described in the disclosure may be useful for navigating the personnel in performing the orthopedics surgery by providing spatial information on the 3D bone image 430, and enabling the personnel to determine appropriate actions during the course of the orthopedics surgery, reducing risks of accidentally damaging the structures covered by the bone 1.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiment(s), it is understood that this disclosure is not limited to the disclosed embodiments but is intended to cover various arrangements included within the spirit and scope of the broadest interpretation so as to encompass all such modifications and equivalent arrangements.

What is claimed is:

1. A system for creating a three-dimensional (3D) bone image of a bone to assist orthopedics surgery, the system to be used with a 3D bone model of the bone, the 3D bone model being constructed by scanning the bone using X-ray computed tomography, the 3D bone model including a plurality of bony landmarks, the bone being placed with a plurality of positioning components that correspond respectively with the bony landmarks, the system comprising:
    a 3D scanning device to scan the bone and to generate a bone contour image; and
    an image processing device that is coupled to the 3D scanning device for receiving the bone contour image, and that includes
        a positioning unit to process the 3D bone model so as to obtain a plurality of spatial locations respectively of the bony landmarks, and to process the bone contour image so as to identify a plurality of features that correspond respectively with the bony landmarks and to obtain a plurality of spatial locations respectively of the features,
        an image alignment unit to perform image registration for the 3D bone model and the bone contour image by aligning the spatial locations of the bony landmarks respectively with the spatial locations of the features, so as to create the 3D bone image by proportionally overlapping the 3D bone model and the bone contour image, and
        a display unit to display the 3D bone image;
    wherein said positioning unit is configured to obtain the spatial locations of the features based on locations respectively of the positioning components.

2. The system of claim 1, wherein said display unit is further to display the bone contour image, and said image processing device further includes a marking unit that is user-operable to mark the features on the bone contour image displayed by said display unit.

3. The system of claim 1, wherein said positioning unit is configured to identify the features by analyzing the bone contour image according to shapes respectively of the bony landmarks.

4. The system of claim 1, the 3D bone model including an image of underlying structure, the bone having a depressed area generated due to the orthopedics surgery, wherein said image processing device further includes:
    a contour analysis unit configured to process the bone contour image so as to indicate an operation surface corresponding with a contour of the depressed area on the 3D bone image;
    a direction analysis unit configured to determine a direction of the image of underlying structure with respect to the operation surface, and that to generate direction data regarding the direction of the image of underlying structure; and
    a distance analysis unit configured to determine distance data regarding a distance between the image of underlying structure and the operation surface based on the direction data.

5. The system of claim 4, wherein:
    said contour analysis unit is configured to partition the operation surface into a plurality of monitoring sectors; and
    said distance analysis unit includes a shortest-distance analyzing module that is configured to obtain a plurality of shortest distances between the image of underlying structure and the operation surface respectively from the monitoring sectors, and the distance data includes the shortest distances.

6. The system of claim 5, wherein said structure distance analysis unit further includes a distance alert module that is configured to compare the shortest distances with a preset alert distance, and to display, for each of the monitoring sectors, a visible cue on the monitoring sector when the shortest distance corresponding thereto is smaller than the preset alert distance.

7. The system of claim 6, wherein the visible cue uses one of different colors and difference brightness intensities to indicate different values of the shortest distance between the monitoring sector and the image of underlying structure.

8. The system of claim 4, wherein:
said contour analysis unit is configured to partition the operation surface into a plurality of monitoring sectors;
said distance analysis unit includes
a vertical distance analyzing module that is configured to obtain a plurality of vertical distances between the image of underlying structure and the operation surface respectively from the monitoring sectors, and
a horizontal distance analyzing module that is configured to obtain a plurality of horizontal distances between the image of underlying structure and the operation surface respectively from the monitoring sectors; and
the distance data includes the vertical distances and the horizontal distances.

9. The system of claim 8, wherein said structure distance analysis unit further includes a distance alert module that is configured to compare each of the vertical distances and the horizontal distances with a preset alert distance, and to display, for each of the monitoring sectors, a visible cue on the monitoring sector when one of the vertical distance and the horizontal distance corresponding thereto is smaller than the preset alert distance.

10. The system of claim 9, wherein the visible cue uses one of different colors and different brightness intensities to indicate different values of said one of the vertical distance and the horizontal distance.

11. The system of claim 4, further comprising a tagging component that is to be placed on the depressed area, wherein:
said 3D scanning device is configured to scan said tagging component along with the bone to generate the bone contour image to contain an image of said tagging component;
said positioning unit is configured to identify the image of said tagging component in the bone contour image, so that the three-dimensional bone image generated by said image processing device contains the image of said tagging component;
said positioning unit is configured to obtain a location of the image of said tagging component; and
said distance analysis unit is further configured to determine a distance between the image of underlying structure and the image of said tagging component based on the location of the image of said tagging component and to indicate the distance between the image of underlying structure and the image of said tagging component in the 3D bone image.

12. The system of claim 4, wherein said image processing device further includes a timer that is configured to control said 3D scanning device to periodically scan the bone and generate the bone contour image, and to control said image processing device to periodically create the 3D bone image based on the bone contour image.

13. A method for creating a three-dimensional bone image of a bone to assist orthopedics surgery, the method to be implemented by a system used with a 3D bone model of the bone, the 3D bone model constructed based on a bone using X-ray computed tomography, the system including a three-dimensional scanning device and an image processing device, the 3D bone model including a plurality of bony landmarks, the method comprising:
processing, by the image processing device, the 3D bone model to obtain a plurality of spatial location for the bony landmarks, respectively;
scanning, by the 3D scanning device, the bone to generate a bone contour image;
processing, by the image processing device, the bone contour image so as to identify a plurality of features that correspond respectively with the bony landmarks, and obtain a plurality of spatial locations respectively of the features;
performing, by the image processing device, image registration for the 3D bone model and the bone contour image by aligning the spatial locations of the bony landmarks respectively with the spatial locations of the features, so as to create the 3D bone image by proportionally overlapping the 3D bone model and the bone contour image; and
displaying, by a display unit of the image processing device, the bone contour image;
wherein the processing of the bone contour image includes, in response to a user-input marking signal on a spot of the display unit indicating one of the features, obtaining a spatial location corresponding with the spot of the display unit as the spatial location of the one of the features.

14. The method of claim 13, wherein the processing of the bone contour image includes identifying the features by analyzing the bone contour image according to shapes respectively of the bony landmarks.

15. The method of claim 13, the bone being placed with a plurality of positioning components that correspond respectively with the bony landmarks,
wherein the processing of the bone contour image includes obtaining the spatial locations of the features based on locations respectively of the positioning components.

16. The method of claim 13, the 3D bone model including an image of underlying structure, the bone having a depressed area generated due to the orthopedics surgery, wherein the processing of the bone contour image further includes:
indicating an operation surface corresponding with a contour of the depressed area on the 3D bone image;
determining a direction of the image of underlying structure with respect to the operation surface, and generating direction data regarding the direction of the image of underlying structure; and
determining distance data regarding a distance between the image of underlying structure and the operation surface based on the direction data.

17. The method of claim 16, wherein:
the processing of the bone contour image further includes partitioning the operation surface into a plurality of monitoring sectors;
the method further comprises obtaining a plurality of shortest distances between the image of underlying structure and the operation surface respectively from the monitoring sectors, the distance data including the shortest distances.

18. The method of claim 16, wherein:

the processing of the bone contour image further includes partitioning the operation surface into a plurality of monitoring sectors;

the method further comprises obtaining a plurality of vertical distances between the image of underlying structure and the operation surface respectively from the monitoring sectors, and a plurality of horizontal distances between the image of underlying structure and the operation surface respectively from the monitoring sectors, the distance data including the vertical distances and the horizontal distances; and comparing each of the vertical distances and the horizontal distances with a preset alert distance, and displaying, for each of the monitoring sectors, a visible cue on the monitoring sector when one of the vertical distance and the horizontal distance corresponding thereto is smaller than the preset alert distance.

19. The method of claim 18, wherein the visible cue uses one of different colors and different brightness intensities to indicate different values of the shortest distance between the monitoring sector and the image of underlying structure.

* * * * *